US011576701B2

(12) United States Patent
Lobo et al.

(10) Patent No.: US 11,576,701 B2
(45) Date of Patent: Feb. 14, 2023

(54) SURGICAL ACCESS ASSEMBLY HAVING A PUMP

(71) Applicant: Covidien LP, Mansfield, MA (US)

(72) Inventors: Astley C. Lobo, West Haven, CT (US); Kevin Desjardin, Prospect, CT (US); Christopher A. Tokarz, Torrington, CT (US); Douglas M. Pattison, East Hartford, CT (US)

(*) Notice: Subject to any disclaimer, the term of this patent is extended or adjusted under 35 U.S.C. 154(b) by 371 days.

(21) Appl. No.: 16/809,632

(22) Filed: Mar. 5, 2020

(65) Prior Publication Data

US 2021/0275215 A1    Sep. 9, 2021

(51) Int. Cl.
*A61B 17/34* (2006.01)
*A61B 1/00* (2006.01)
*A61B 1/313* (2006.01)

(52) U.S. Cl.
CPC ........ *A61B 17/3423* (2013.01); *A61B 1/3132* (2013.01); *A61B 17/3498* (2013.01); *A61B 2017/3486* (2013.01)

(58) Field of Classification Search
CPC ............ A61B 17/3423; A61B 17/3498; A61B 2017/3486; A61B 1/3132; A61B 1/32; A61B 8/04; A61M 2205/075; A61M 2205/128
See application file for complete search history.

(56) References Cited

U.S. PATENT DOCUMENTS

| 451,179 | A | * | 4/1891 | Ware ........................ A61M 1/06 92/92 |
|---|---|---|---|---|
| 3,402,710 | A | | 9/1968 | Paleschuck |
| 3,495,586 | A | | 2/1970 | Regenbogen |
| 4,016,884 | A | | 4/1977 | Kwan-Gett |
| 4,102,342 | A | * | 7/1978 | Akiyama ........ A61M 25/10183 604/920 |
| 4,112,932 | A | | 9/1978 | Chiulli |
| 4,183,357 | A | | 1/1980 | Bentley et al. |
| 4,356,826 | A | | 11/1982 | Kubota |
| 4,402,683 | A | | 9/1983 | Kopman |
| 4,653,476 | A | | 3/1987 | Bonnet |
| 4,737,148 | A | | 4/1988 | Blake |
| 4,863,430 | A | | 9/1989 | Klyce et al. |

(Continued)

FOREIGN PATENT DOCUMENTS

| CA | 2702419 A1 | 11/2010 |
|---|---|---|
| EP | 0226026 A2 | 6/1987 |

(Continued)

*Primary Examiner* — Kevin T Truong
*Assistant Examiner* — Tracy L Kamikawa
(74) *Attorney, Agent, or Firm* — Carter, DeLuca & Farrell LLP (57) ABSTRACT

A surgical access assembly including an elongated cannula member having proximal and distal end portions, a cannula housing coupled to the proximal end portion of the elongated cannula member, a balloon anchor coupled to the distal end portion of the elongated cannula member, and a collar disposed along the elongated cannula member and in fluid communication with the balloon anchor. The collar includes a first check valve and a manually actuatable pump. The first check valve is configured to control flow of air into the balloon anchor. The manually actuatable pump is coupled to the first check valve.

20 Claims, 9 Drawing Sheets

(56) References Cited

U.S. PATENT DOCUMENTS

| | | |
|---|---|---|
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,812 A | 2/1999 | Correia |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,036,711 A | 3/2000 | Mozdzierz et al. |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |

(56) References Cited

U.S. PATENT DOCUMENTS

| | | |
|---|---|---|
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,744,617 B2* | 6/2010 | Lunsford ............ A61B 1/00082 |
| | | 600/184 |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 7,998,113 B2* | 8/2011 | Swisher ................ A61M 25/04 |
| | | 604/101.05 |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2* | 11/2011 | Hart ................... A61B 17/3421 |
| | | 604/164.04 |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,382,707 B2* | 2/2013 | Albrecht ............... A61M 25/04 |
| | | 604/164.02 |

(56) References Cited

U.S. PATENT DOCUMENTS

| | | |
|---|---|---|
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 10,675,056 B2 | 6/2020 | Tokarz |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111052 A1 | 6/2004 | Moenning |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0047185 A1 | 3/2006 | Shener |
| 2006/0071432 A1 | 4/2006 | Staudner |
| 2006/0079922 A1* | 4/2006 | Creston ............ A61B 17/3421 606/167 |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0197969 A1* | 8/2007 | Hillborg ............ A61B 5/021 604/142 |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0200871 A1* | 8/2008 | Slater ............... A61M 25/0097 604/96.01 |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |

(56) References Cited

U.S. PATENT DOCUMENTS

| | | |
|---|---|---|
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2020/0022726 A1* | 1/2020 | Mikol ............ A61B 17/3498 |
| 2020/0107859 A1* | 4/2020 | Zhu .................. A61B 17/3498 |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 A2 | 3/2011 |
| EP | 2343019 | 7/2011 |
| GB | 2469083 | 4/2009 |
| WO | 84/01512 A1 | 4/1984 |
| WO | 9314801 A1 | 8/1993 |
| WO | 9404067 A1 | 3/1994 |
| WO | 9610963 A1 | 4/1996 |
| WO | 9636283 A1 | 11/1996 |
| WO | 9733520 A1 | 9/1997 |
| WO | 9742889 A1 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 A2 | 2/2001 |
| WO | 0149363 A1 | 7/2001 |
| WO | 0207611 A2 | 1/2002 |
| WO | 03034908 A2 | 5/2003 |
| WO | 03071926 | 9/2003 |
| WO | 03077726 | 9/2003 |
| WO | 2004043275 A1 | 5/2004 |
| WO | 2004054456 A1 | 7/2004 |
| WO | 2004075741 A2 | 9/2004 |
| WO | 2004075930 A2 | 9/2004 |
| WO | 2005058409 A1 | 6/2005 |
| WO | 2006019723 | 2/2006 |
| WO | 2006100658 A2 | 9/2006 |
| WO | 2006110733 A2 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 A2 | 6/2008 |
| WO | 2008093313 | 8/2008 |
| WO | 2008103151 A2 | 8/2008 |
| WO | 2008121294 A1 | 10/2008 |
| WO | 2008147644 | 12/2008 |
| WO | 2009036343 A1 | 3/2009 |
| WO | 2010000047 | 1/2010 |
| WO | 2010141409 A1 | 12/2010 |
| WO | 2010141673 A1 | 12/2010 |

* cited by examiner

SURGICAL ACCESS ASSEMBLY HAVING A PUMP

FIELD

The present technology is generally related to surgical access devices and more particularly to a surgical access assembly having a pump for use in a minimally invasive surgical procedure.

BACKGROUND

Minimally invasive surgical procedures including both endoscopic and laparoscopic procedures permit surgery to be performed on organs, tissues, and vessels far removed from an opening within the tissue. In laparoscopic procedures, the abdominal cavity is insufflated with an insufflation fluid, e.g., $CO_2$, to create a pneumoperitoneum thereby providing access to the underlying organs. A laparoscopic instrument is introduced through a cannula accessing the abdominal cavity to perform one or more surgical tasks. An interior of the cannula usually includes a seal to establish a substantially fluid-tight seal about the instrument to preserve the integrity of the pneumoperitoneum.

While minimally invasive surgical procedures have proven to be quite effective in surgery, several limitations remain. For example, the cannula which is subjected to the pressurized environment, i.e., the pneumoperitoneum, may exhibit a tendency to back out of the incision in the abdominal wall particularly during manipulation of the instrument within the cannula. Conventional cannulas may incorporate an inflatable balloon at the end of the cannula in an effort to resist withdrawal of the cannula from the tissue site. A pump may be coupled to the cannula and actuated to either inflate or deflate the balloon.

SUMMARY

The present disclosure relates to a surgical access assembly including a balloon trocar for providing access to a surgical cavity within a patient (e.g., an abdominal cavity) having a pump integrally coupled to a check valve of the balloon trocar for inflating a balloon of the balloon trocar.

In one aspect, the present disclosure provides a surgical access assembly including an elongated cannula member having proximal and distal end portions, a cannula housing coupled to the proximal end portion of the elongated cannula member, a balloon anchor coupled to the distal end portion of the elongated cannula member, and a collar disposed along the elongated cannula member and in fluid communication with the balloon anchor. The collar includes a first check valve and a manually actuatable pump. The first check valve is configured to control flow of air into the balloon anchor. The manually actuatable pump is coupled to the first check valve.

In aspects, the pump may include a second check valve configured to transition between open and closed states to control the flow of air into the pump.

In aspects, one of the first or second check valves may be configured to transition between the open and closed states in response to actuation of the pump.

In aspects, the actuation of the pump may transition the pump between first and second states.

In aspects, transitioning the pump from the first state to the second state may transition the first check valve to the open state and supply air to the balloon anchor.

In aspects, transitioning the pump from the second state to the first state may transition the first check valve to the closed state.

In aspects, the closed state of the second check valve maintains air pressure in the balloon anchor.

In aspects, transitioning the pump to the first state may transition the second check valve to the open state, thereby transferring air into the pump.

In aspects, the collar may include a release valve having a release check valve and a piston. The release check valve is configured to control flow of air out of the balloon anchor. The piston is in communication with the release check valve having a longitudinal tube therethrough.

In aspects, the release check valve may be configured to transition between open and closed states in response to actuation of the piston.

In aspects, the piston may be spring-loaded and configured to transition between expanded state and compressed states.

In aspects, the actuation of the piston may be configured to transition the release check valve to the open state, thereby releasing air from the balloon anchor.

In another aspect, the disclosure provides a method of inflating and deflating a balloon anchor of a surgical access assembly including actuating a pump coupled to a first check valve of the surgical access assembly, supplying air to the balloon anchor, and maintaining air pressure in the balloon anchor.

In aspects, the method may include actuating a release valve coupled to the surgical access assembly and releasing air from the balloon anchor.

In aspects, actuating the pump may include transitioning the pump between first and second states.

In aspects, actuating the release valve may include transitioning the release valve between expanded and compressed states.

In aspects, supplying air to the balloon anchor may include transitioning the pump from a first state to a second state and transitioning the first check valve from a closed state to an open state.

In aspects, maintaining air pressure in the balloon anchor may include transitioning the pump from the second state to the first state and transitioning the first check valve to the closed state.

In aspects, releasing air from the balloon anchor includes transitioning the release valve from an expanded state to a compressed state and transitioning the release check valve of the release valve from a closed state to an open state.

In another aspect, the disclosure provides a surgical access assembly, including a balloon trocar having an elongated cannula member having proximal and distal end portions, a cannula housing having an outer sleeve, the cannula coupled to the proximal end portion of the elongated cannula member, a balloon anchor coupled to the distal end portion of the elongated cannula member. The surgical access assembly also includes a collar disposed along the elongated cannula member and in fluid communication with the balloon anchor. The collar includes a port extending outward from the elongated cannula member, a manually actuatable pump, and a release valve. The port is configured to receive a first check valve configured to control flow of air into the balloon anchor. The manually actuatable pump is coupled to the first check valve. The release valve is coupled to the port and configured to control flow of air out of the balloon anchor.

The details of one or more aspects of the disclosure are set forth in the accompanying drawings and the description

DETAILED DESCRIPTION

Embodiments of the presently disclosed surgical access assembly are described in detail with reference to the drawings, in which like reference numerals designate identical or corresponding elements in each of the several views. As used herein, the term "distal" refers to that portion of the surgical access assembly or component thereof, farther from the user, while the term "proximal" refers to that portion of the surgical access assembly, or component thereof, closer to the user.

As used herein, the term "clinician" refers to a doctor, nurse, surgeon, or other care provider and may include support personnel. In the following description, well-known functions, or construction are not described in detail to avoid obscuring the disclosure in unnecessary detail.

In general, the present disclosure provides a pump for use with a balloon trocar. The pump is configured to integrally couple to a check valve of the trocar balloon. Upon compression and release of the pump, air may enter the balloon of the balloon trocar. Upon depression of a release valve coupled to the balloon trocar, air may be released from the balloon of the balloon trocar. In this way, a clinician may no longer need to attach an extra component to the balloon trocar to inflate or deflate the balloon of the balloon trocar.

Figure 1:
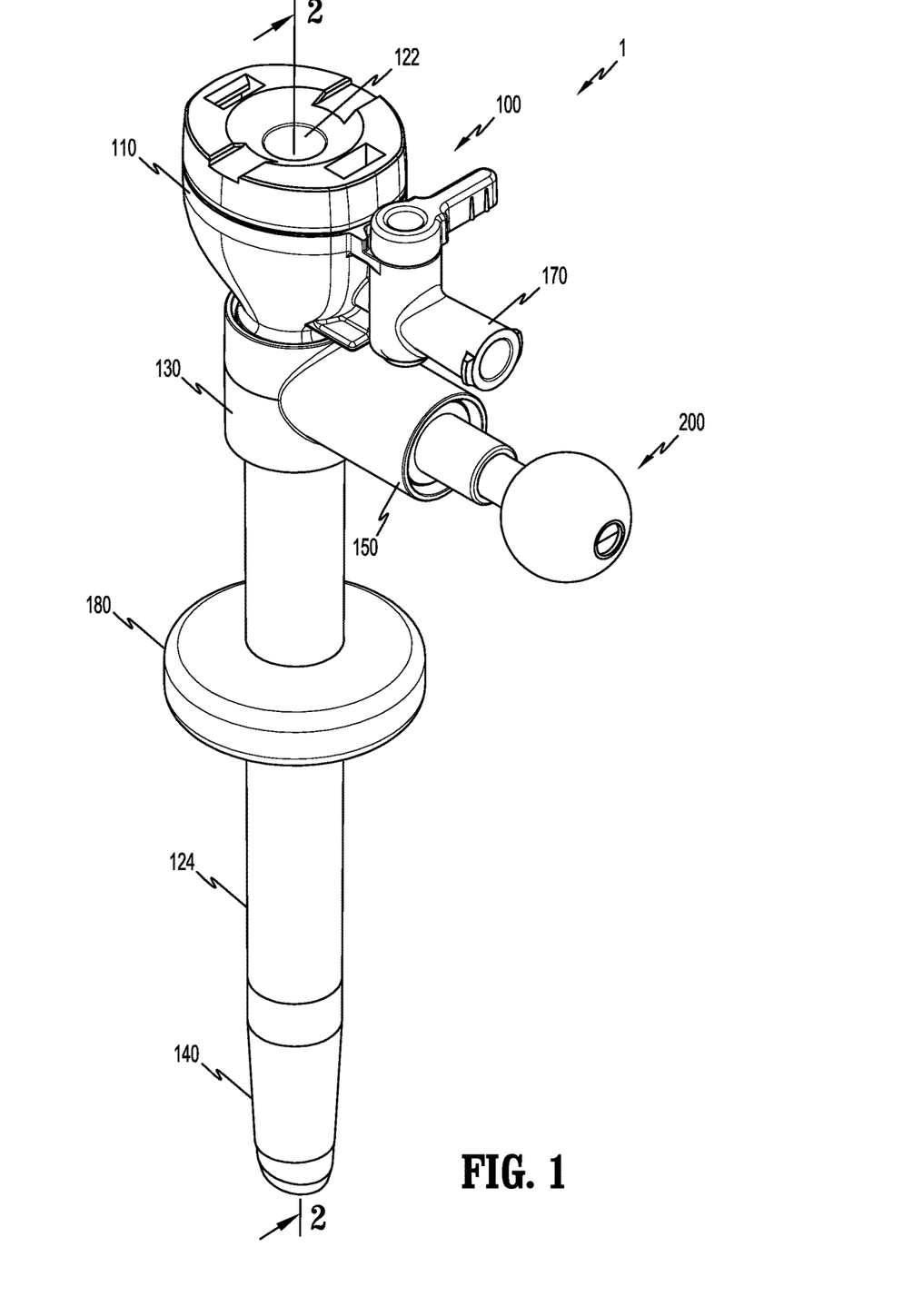
FIG. 1 is a perspective view a surgical access assembly according to an aspect of the disclosure including a cannula, a pump, and a balloon anchor.

Referring initially to FIG. 1, which illustrates a surgical access assembly 1 generally including a surgical cannula assembly or balloon trocar 100, and a manually actuatable pump or pump 200 for use with the balloon trocar 100. The balloon trocar 100 is intended to permit access to an insufflated abdominal cavity during a laparoscopic procedure to permit the introduction of a surgical instrument for performing various surgical tasks on internal organs within the cavity. The surgical instrument may be a surgical instrument such as laparoscopic or endoscopic clip appliers, graspers, dissectors, retractors, staplers, laser probes, photographic devices, tubes, endoscopes and laparoscopes, electro-surgical devices and the like. An obturator (not explicitly shown) may be positioned in the balloon trocar 100 to facilitate access to the abdominal cavity. The obturator may be any conventional obturator having a penetrating tip configured to penetrate tissue.

The balloon trocar 100 includes a cannula housing 110, an elongated cannula member 120 extending distally from the cannula housing 110, an outer sleeve 124 coaxially mounted over the elongated cannula member 120, a first collar 130, a second collar 180, and an expandable member or balloon anchor 140 formed with the outer sleeve 124. The cannula housing 110 is dimensioned for engagement by the clinician and may include or more internal seals (not shown) adapted to establish a seal about a surgical instrument introduced therethrough. The cannula housing 110 also may include an insufflation connector 170 (e.g., a luer connector) for connecting to a source of insufflation fluid (not shown) for delivery within, e.g., the abdominal cavity. The elongated cannula member 120 defines a longitudinal axis X-X along which the elongated cannula member 120 extends. The elongated cannula member 120 defines a longitudinal passageway 122 to permit passage of the surgical instrument. The longitudinal passageway 122 is also in fluid communication with the insufflation connector 170 to convey insufflation fluids into the abdominal cavity to establish and/or maintain the pneumoperitoneum.

Figures 2, 3:
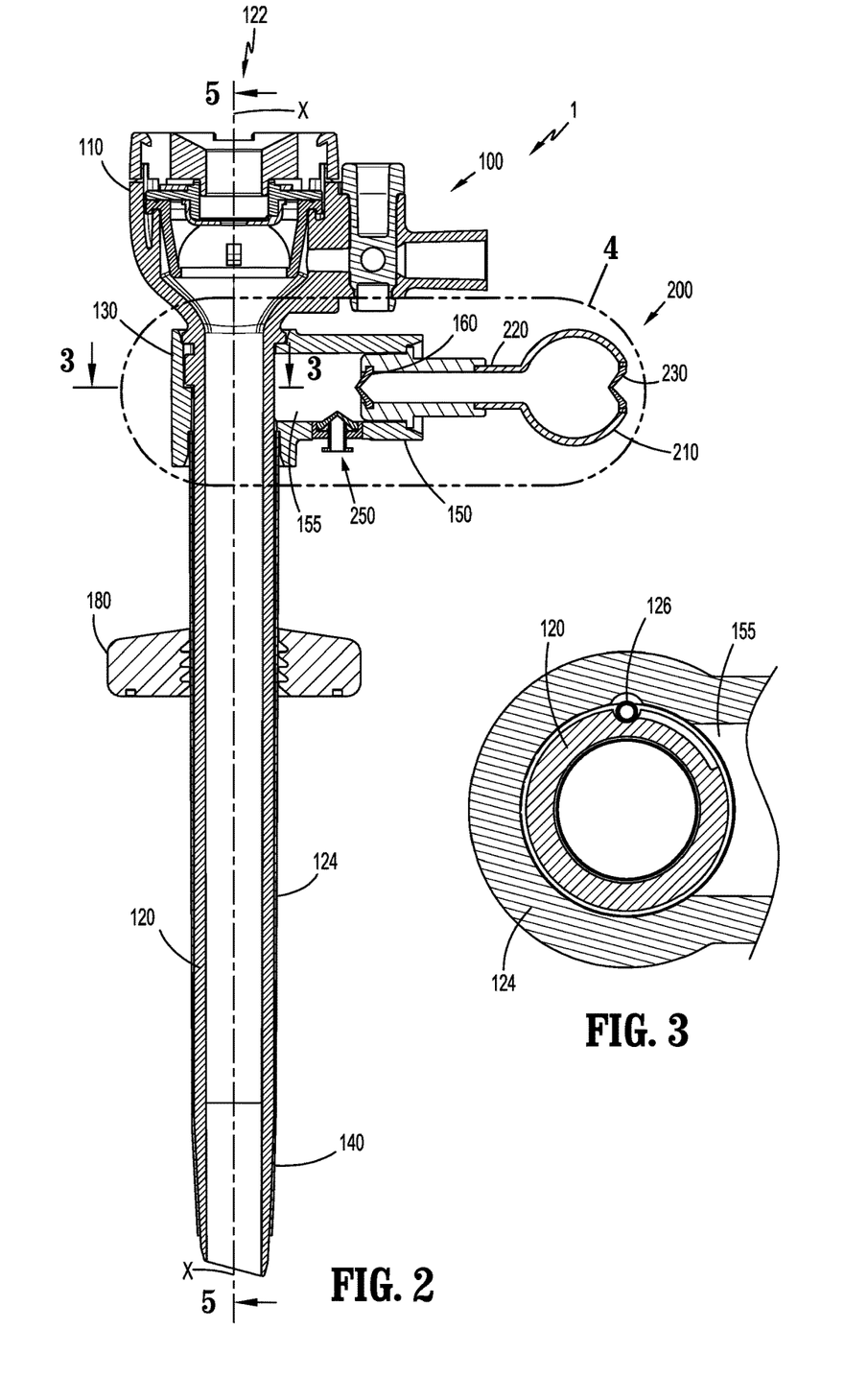
FIG. 2 is a side cross-sectional view taken along section line 2-2 of FIG. 1.
FIG. 3 is an enlarged top cross-sectional view taken along section line 3-3 of FIG. 2.
Figure 5:
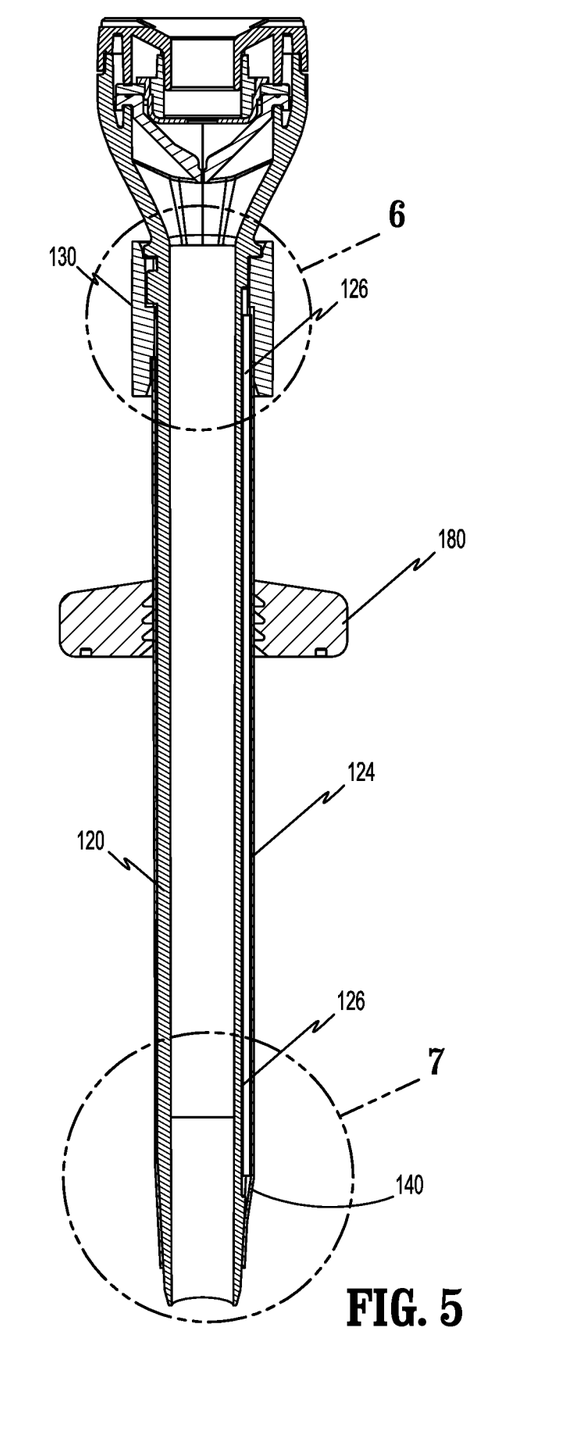
FIG. 5 is a side cross-sectional view taken along section line 5-5 of FIG. 2.
Figure 6:
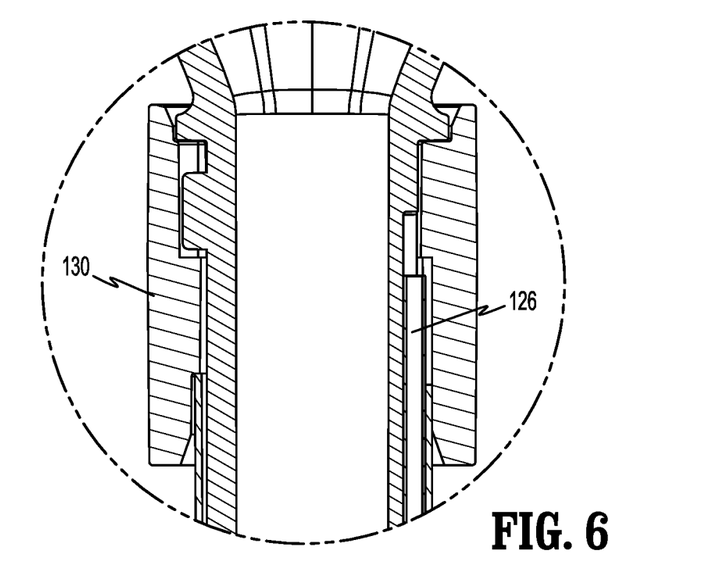
FIG. 6 is an enlarged view of the area of detail indicated in FIG. 5.
Figure 7:
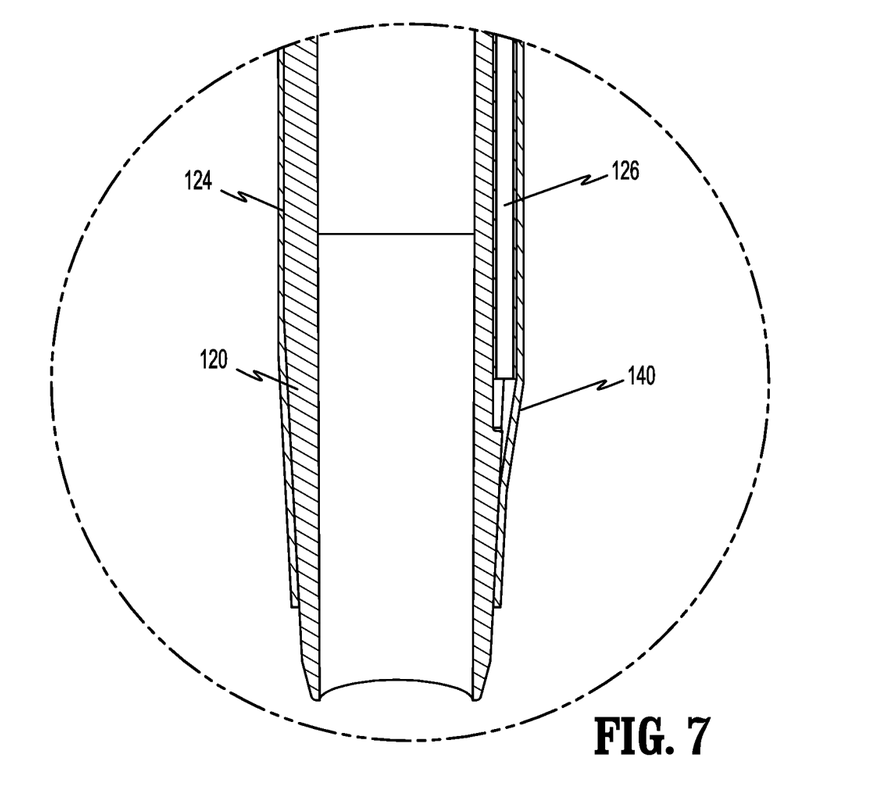
FIG. 7 is an enlarged view of the area of detail indicated in FIG. 5.

With reference to FIG. 2, the first collar 130 of the balloon trocar 100 is positioned adjacent to the cannula housing 110 about the proximal end portion of the elongated cannula member 120. The first collar 130 has a tube or port 150 extending laterally outward therefrom and configured to allow for inflow and outflow of air. The port 150 is dimensioned to receive a first check valve 160 and defines a chamber 155, which is in communication with the balloon anchor 140. The port 150 and the first check valve 160 may be ultrasonically welded together or mechanically engaged in some other fashion, e.g., snap-fit, adhesive, etc. With quick reference to FIG. 5, a lumen 126 of the surgical access assembly 1 extends from the first collar 130 (FIG. 6) distally towards the balloon anchor 140 (FIG. 7). The lumen 126, in some instances, may be a groove along the elongated cannula member 120.

The first check valve 160 is configured to transition between open and closed states in response to actuation of the pump 200, as will be described hereinbelow. In aspects, the first check valve 160 may be any suitable type of valve, such as, for example, a diaphragm check valve, a swing check valve, a ball check valve, an in-line check valve, or a lift-check valve.

Figure 4:
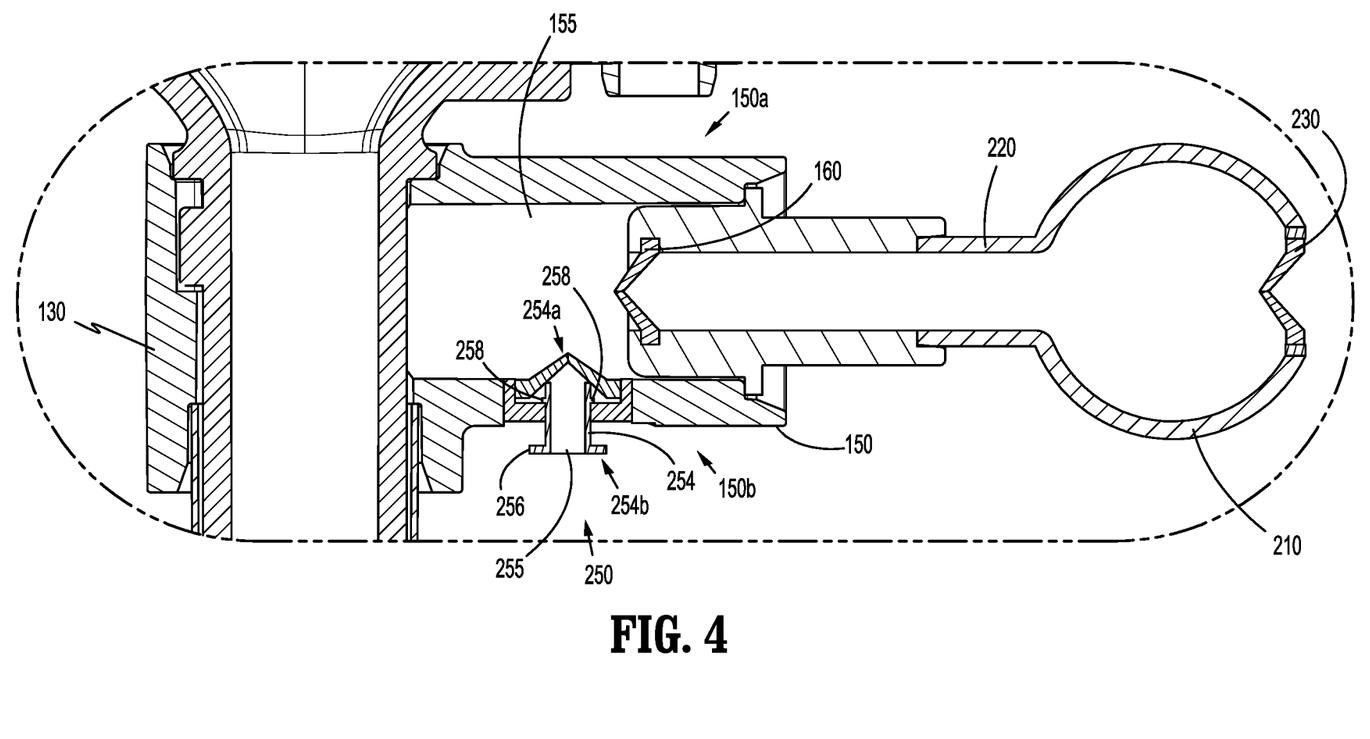
FIG. 4 is an enlarged view of the area of detail indicated in FIG. 2.

With reference to FIG. 4, the pump 200 of the surgical access assembly 1 is coupled to the port 150 and configured to control the flow of air into the balloon anchor 140. The pump 200 includes a bulbous portion 210 and a shaft portion 220 which are monolithically formed. The port 150 of the first collar 130 is dimensioned to receive and integrally mate with the shaft portion 220 portion of the pump 200. The shaft portion 220 of the pump 200 and the port 150 may be ultrasonically welded together or mechanically engaged in some other fashion, e.g., snap-fit, adhesive, etc. The bulbous portion 210 of the pump 200, when actuated, is configured to be transition between first and second states. In aspects, the bulbous portion 210 of the pump 200 is soft and malleable and may be formed of any material with sufficient flex to allow for the transition between first and second states, such as, for example, rubber, silicone, vinyl, or neoprene. In aspects, the bulbous portion 210 may assume any shape suitable for depression and retention of air. In aspects, bulbous portion 210 of the pump may include a second check valve 230. The second check valve 230 is configured to transition between open (FIG. 9) and closed (FIG. 4) states in response to actuation of the pump 200 to allow air from the surrounding environment to enter the pump 200. In aspects, the second check valve 230 may be any suitable type of valve, such as, for example, a diaphragm check valve, a swing check valve, a ball check valve, an in-line check valve, a lift-check valve, or a stop-check valve.

The port 150 further includes a release valve 250 disposed along a bottom end portion 150*b* of the port 150 and in communication with the chamber 155 to control the flow of air out of the balloon anchor 140. The release valve 250 includes a release check valve 252 and a piston 254. The release check valve 252 is configured to transition between open (FIG. 12) and closed (FIG. 4) states in response to actuation of the release valve 250. In aspects, the release check valve 252 may be any suitable type of valve, such as, for example, a diaphragm check valve, a swing check valve, a ball check valve, an in-line check valve, or a lift-check valve. In aspects, the release valve 250 may be a quick release button configured to open the first check valve 160 and the second check valve 230. Thus, allowing air to be released from the balloon anchor 140 out the second check valve 230 of the pump 200 via the lumen 126, the chamber 155, and the first check valve.

The piston 254 includes a longitudinal tube 255, a base, and stops 258, disposed along an outer surface of the piston 254. The stops 258 are disposed on each side of the outer surface of the piston 254 towards a proximal end portion 254*a* of the piston 254 and configured to prevent the piston 254 from being removed from the release valve 250. The base 256 having an opening is monolithically coupled to a distal end portion 254*b* of the piston 254, to provide a surface for a clinician to depress and permit the outflow of air from the chamber 155 via the longitudinal tube 255 of the piston 254. The bottom end portion 150*b* of the port 150 is dimensioned to receive the piston 254, which is spring-loaded and configured to transition the spring-loaded piston 254, biased towards the expanded state, between expanded and compressed state upon actuation of the piston 254.

In operation, the surgical access assembly 1 may be used in a minimally invasive surgery to provide access to an underlying cavity, e.g., an abdominal cavity. In one methodology, the abdominal cavity 30 is insufflated to establish a pneumoperitoneum. The obturator is positioned within the balloon trocar 100 and the assembled unit is advanced, while the balloon anchor 140 is in a deflated state, through a first layer of tissue 10 and a second layer of tissue 20, until the second collar 180 engages the first layer of tissue 10 (FIG. 11).

Figure 8:
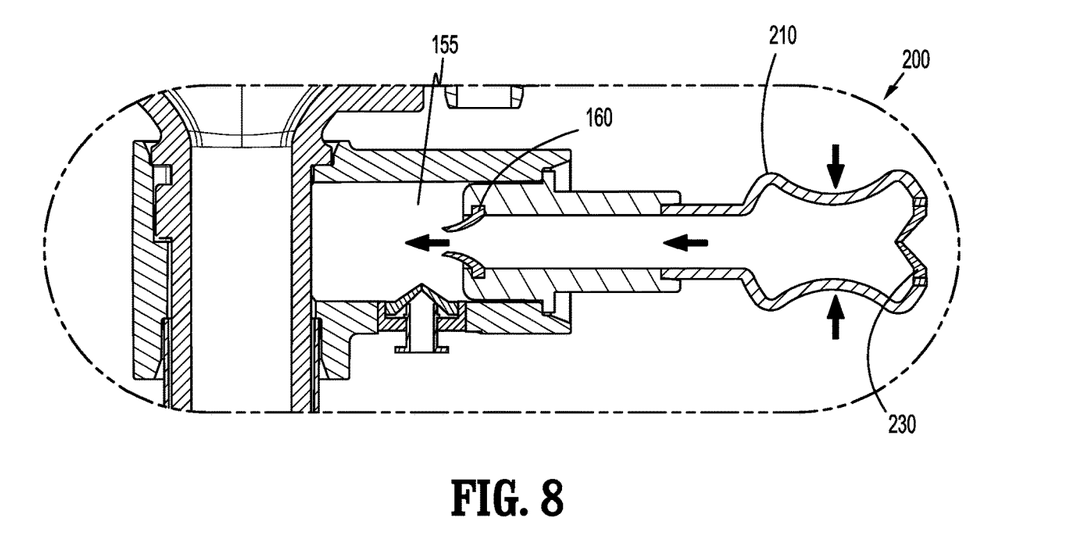
FIG. 8 is the view of the area of detail indicated in FIG. 2, with the pump in a first state.
Figure 9:
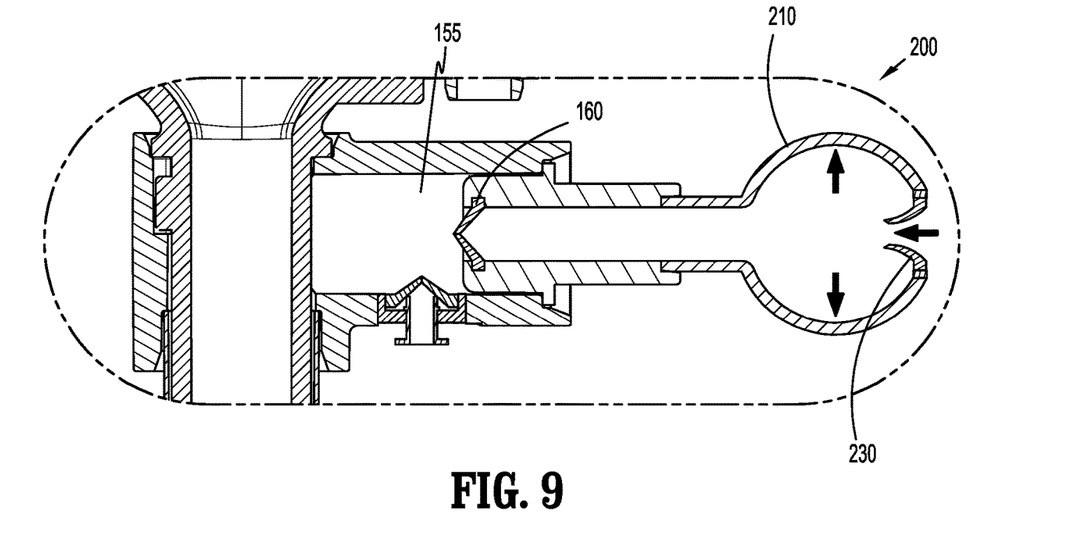
FIG. 9 is the view of the area of detail indicated in FIG. 2, with the pump in a second state.
Figure 10:
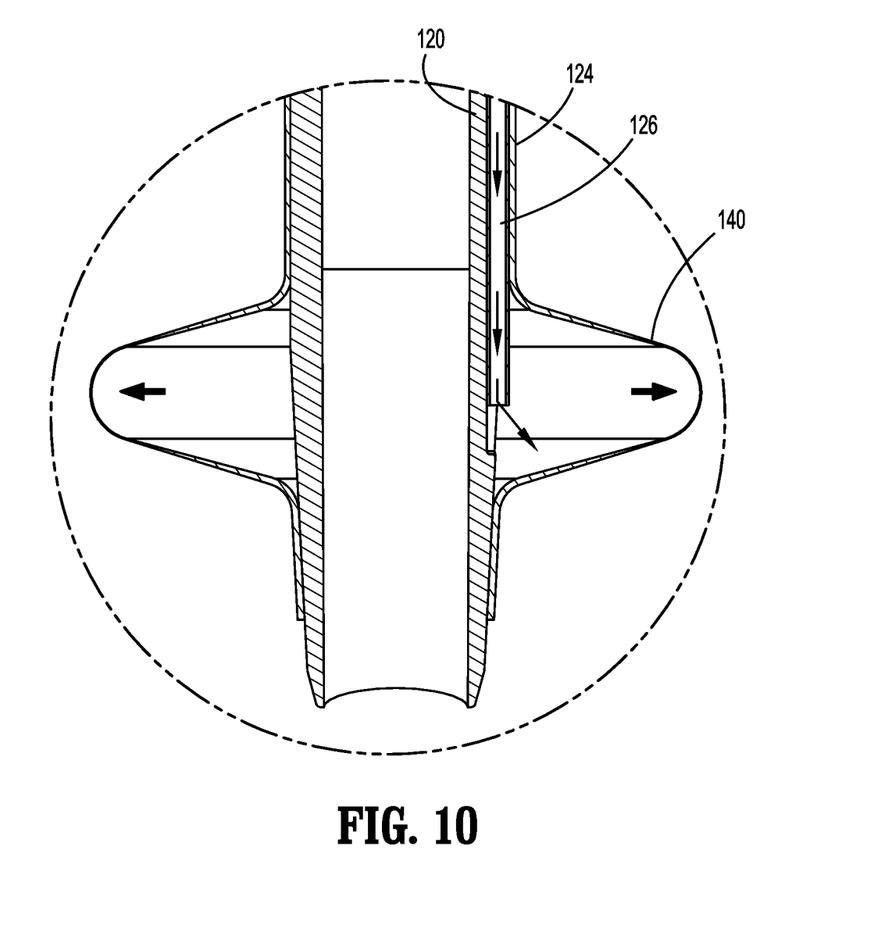
FIG. 10 illustrates the inflated balloon anchor of FIG. 7.
Figure 11:
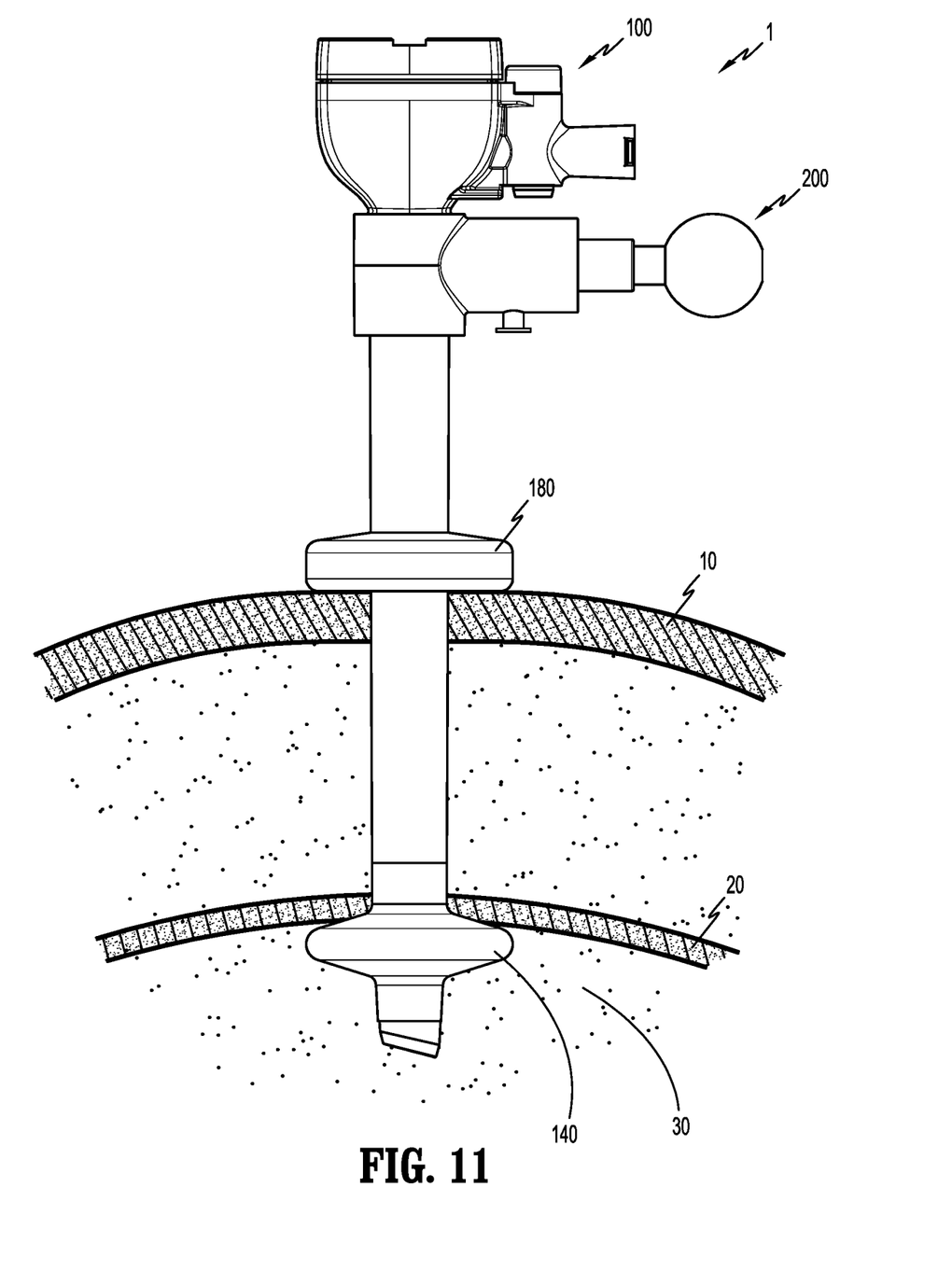
FIG. 11 is a side view of the surgical access assembly of FIG. 1, wherein the surgical access assembly is inserted into a patient and the balloon anchor is inflated.

Referring now to FIGS. 8-11, upon positioning the balloon anchor 140 adjacent the abdominal wall, the bulbous portion 210 of the pump 200 is actuated, transitioning the pump 200 from the first state to the second state. Upon the pump 200 transitioning from the first state to the second state, the first check valve 160 is transitioned from the closed state (FIG. 9) to the open state (FIG. 8), thereby supplying air to the balloon anchor 140. The air is transferred from the pump 200 to the chamber 155 and through the lumen 126 (FIG. 8). The air is transferred from the lumen 126 to the balloon anchor 140, causing the balloon anchor 140 expand and inflate (FIG. 10). Once air is supplied to the balloon anchor 140, the pump 200 is transitioned from the second state (FIG. 8) to the first state (FIG. 9) and the first check valve 160 is transitioned from the open state (FIG. 8) to the closed state (FIG. 9), thus maintaining air pressure in the balloon anchor 140 (FIG. 9). Air pressure is maintained in the balloon anchor 140, through the lumen 126 to the chamber 155. In aspects, upon transitioning the pump from the second state to the first state, the second check valve 230 is transitioned from the closed state to the open state, thus supplying air from the surrounding environment into the pump 200. The air from the surrounding environment fills the pump 200 with air, and the air pressure in the pump 200 thereby causes the second check valve 230 to transition from the open state to the closed state. In aspects, the pump 200 may be rapidly transitioned between the first state and the second state, until the balloon anchor 140 is inflated to a desire size. In the inflated or at least partially inflated state, the balloon anchor 140 will resist withdrawal of the balloon trocar 100 from the abdominal cavity 30 while also providing a seal within the internal surface of the second layer of tissue 20, minimizing passage of fluids, including inflation fluids, from the abdominal cavity 30 (FIG. 11).

Figure 12:
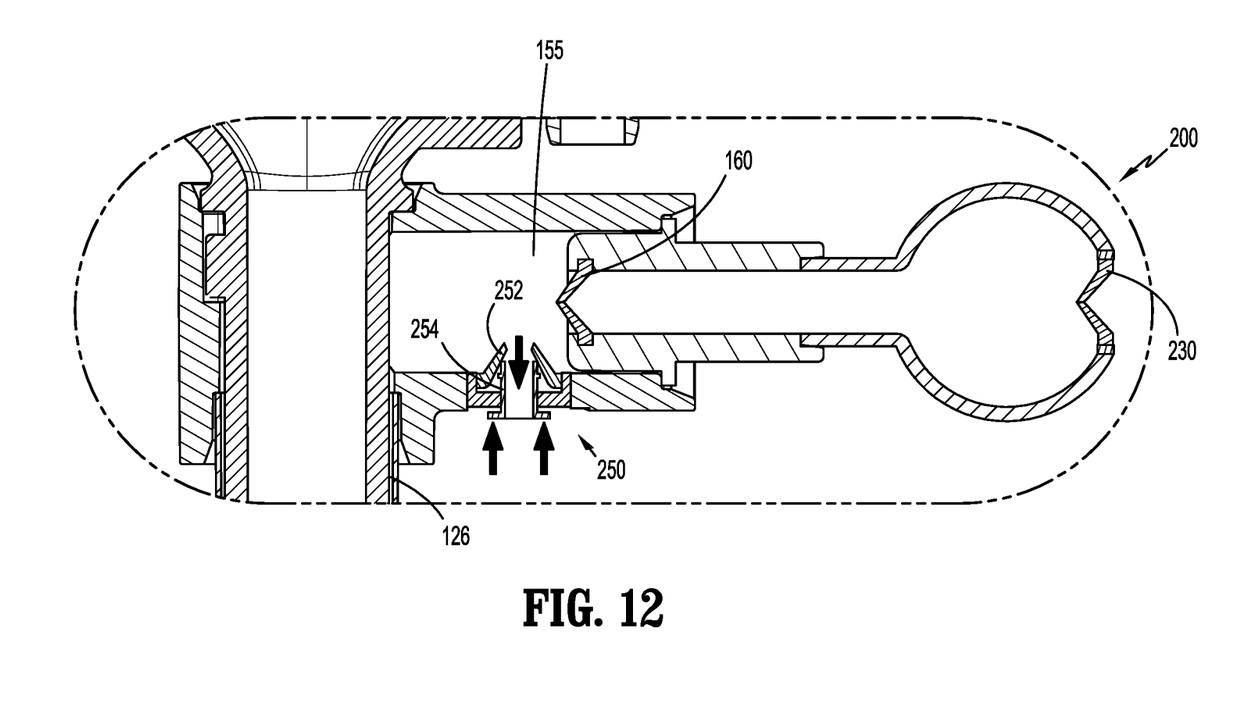
FIG. 12 is an enlarged view of the area of detail indicated in FIG. 2, wherein a release valve is actuated to a compressed state.

Referring to FIG. 12, to deflate and withdraw the balloon trocar 100 from the abdominal cavity 30, the release valve 250 is actuated transitioning the release valve 250 from the expanded state (FIG. 4) to the compressed state. Once the release valve 250 is in the compressed state, the piston 254 engages the release check valve 252 transitioning the release check valve 252 from the closed state to the open state. Upon, transitioning the release check valve 252 to the open state, air is released from the balloon anchor 140 through the lumen 126 (FIG. 5) into the chamber 155 and out the release valve 250 (FIG. 12). In aspects, the release valve 250 is transitioned to the compressed state and held until the balloon anchor 140 is fully deflated or at least partially deflated to allow for removal of the balloon trocar 100. In aspects, the release valve 250 is actuated and held, transitioning the first check valve 160 and the second check valve 230 from the closed position to the open position until the balloon anchor 140 is fully deflated or at least partially deflated to allow for removal of the balloon trocar 100. Once deflated, the balloon trocar 100 may be withdrawn from the second layer of tissue 20 and the first layer of tissue 10.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A surgical instrument comprising:
   an elongated tubular member;
   a balloon anchor coupled to a distal portion of the elongated tubular member; and
   a collar disposed on the elongated tubular member and in fluid communication with the balloon anchor, the collar including:
   a port having a check valve configured to control fluid flow into the balloon anchor;
   a pump coupled to the port; and a release valve configured to control fluid flow out of the balloon anchor, the release valve including a piston having a tube extending through the piston.

2. The surgical instrument of claim 1, wherein the release valve is disposed along a bottom end portion of the port.

3. The surgical instrument of claim 2, wherein the release valve is in communication with a chamber to control the fluid flow out of the balloon anchor.

4. The surgical instrument of claim 3, wherein actuation of the release valve transitions the release valve between open and closed states.

5. The surgical instrument of claim 1, wherein the piston further includes:
   a base; and
   a stop disposed on an outer surface of the piston and positioned on a proximal end portion of the piston.

6. The surgical instrument of claim 5, wherein the base of the piston has an opening and is monolithically coupled to a distal end portion of the piston.

7. The surgical instrument of claim 6, wherein the base of the piston permits fluid flow from a chamber through the tube of the piston.

8. The surgical instrument of claim 5, wherein the stop of the piston maintains the piston in the release valve.

9. A surgical access assembly comprising:
   an elongated cannula member having proximal and distal end portions;
   a cannula housing coupled to the proximal end portion of the elongated cannula member;
   a balloon anchor coupled to the distal end portion of the elongated cannula member; and
   a collar disposed along the elongated cannula member and in fluid communication with the balloon anchor, the collar including:
      a first check valve configured to control flow of air into the balloon anchor;
      a manually actuatable pump coupled to the first check valve;
      a release check valve configured to control flow of air out of the balloon anchor; and
      a piston including a longitudinal tube extending through the piston, the piston in communication with the release check valve.

10. The surgical access assembly of claim 9, wherein the pump further includes a second check valve configured to transition between open and closed states to control the flow of air into the pump.

11. The surgical access assembly of claim 10, wherein one of the first or second check valves is configured to transition between respective open and closed states in response to actuation of the pump.

12. The surgical access assembly of claim 9, wherein actuation of the pump transitions the pump between first and second states.

13. The surgical access assembly of claim 12, wherein transitioning the pump from the first state to the second state transitions the first check valve to an open state and supplies air to the balloon anchor.

14. The surgical access assembly of claim 13, wherein transitioning the pump from the second state to the first state transitions the first check valve to a closed state.

15. The surgical access assembly of claim 14, wherein the closed state of the first check valve maintains air pressure in the balloon anchor.

16. The surgical access assembly of claim 14, wherein transitioning the pump to the first state transitions a second check valve to an open state, thereby transferring air into the pump.

17. The surgical access assembly of claim 9, wherein the release check valve is configured to transition between open and closed states in response to actuation of the piston.

18. The surgical access assembly of claim 17, wherein the actuation of the piston is configured to transition the release check valve to the open state, thereby releasing air from the balloon anchor causing the balloon anchor to deflate.

19. The surgical access assembly of claim 9, wherein the piston is spring-loaded and configured to transition between expanded and compressed states.

20. A surgical access assembly, comprising:
   a balloon trocar including:
      an elongated cannula member having proximal and distal end portions;
      a cannula housing having an outer sleeve, the cannula housing coupled to the proximal end portion of the elongated cannula member;
      a balloon anchor coupled to the distal end portion of the elongated cannula member; and
      a collar disposed along the elongated cannula member and in fluid communication with the balloon anchor, the collar including:
         a port extending outward from the elongated cannula member, the port configured to receive a first check valve configured to control flow of air into the balloon anchor;
         a manually actuatable pump coupled to the first check valve;
         a release valve coupled to the port and configured to control flow of air out of the balloon anchor; and
         a piston including a longitudinal tube extending through the piston, the piston in communication with the release check valve.

* * * * *